(12) United States Patent
Yoo et al.

(10) Patent No.: US 7,591,943 B2
(45) Date of Patent: Sep. 22, 2009

(54) PROCESS FOR THE REDUCTION OF SULFUR, NITROGEN AND THE PRODUCTION OF USEFUL OXYGENATES FROM HYDROCARBON MATERIALS VIA ONE-POT SELECTIVE OXIDATION

(75) Inventors: Jin S. Yoo, Flossmoor, IL (US); Sang-Chul Lee, Asan-si (KR); Ho Dong Kim, Gangneung-si (KR)

(73) Assignee: Kocat Inc., Seoul (KR)

( * ) Notice: Subject to any disclaimer, the term of this patent is extended or adjusted under 35 U.S.C. 154(b) by 169 days.

(21) Appl. No.: 11/858,449

(22) Filed: Sep. 20, 2007

(65) Prior Publication Data

US 2008/0121565 A1     May 29, 2008

Related U.S. Application Data

(60) Provisional application No. 60/851,052, filed on Oct. 12, 2006.

(30) Foreign Application Priority Data

Jun. 11, 2007    (KR) .................. 10-2007-0056781
Jun. 25, 2007    (KR) .................. 10-2007-0062496
Aug. 6, 2007    (KR) .................. 10-2007-0078542

(51) Int. Cl.
*C10G 27/04*     (2006.01)
*C10G 45/04*     (2006.01)

(52) U.S. Cl. .................. 208/208 R; 208/243; 208/244; 208/249; 208/295; 562/412; 562/413

(58) Field of Classification Search ............ 208/208 R, 208/243–244, 295; 562/412–413
See application file for complete search history.

(56) References Cited

U.S. PATENT DOCUMENTS

| | | | |
|---|---|---|---|
| 6,175,038 B1* | 1/2001 | Jhung et al. .................. 562/412 |
| 6,180,822 B1* | 1/2001 | Jhung et al. .................. 562/412 |
| 6,194,607 B1* | 2/2001 | Jhung et al. .................. 562/412 |
| 6,448,436 B1* | 9/2002 | Kreitman et al. ............. 562/412 |

OTHER PUBLICATIONS

Park, S-E et al (2004). Studies in Surface Science and Catalysis, 153, 303-314.*
Jhung, S.H. et al (2002). Applied Catalysis A, 230, 31-40.*
Yoo, J.S. et al (2002). Applied Catalysis A, 223, 239-251.*
Baek, S-C et al (2003), Applied Catalysis A, 244, 19-25.*

* cited by examiner

*Primary Examiner*—Robert J Hill, Jr.
*Assistant Examiner*—Brian McCaig
(74) *Attorney, Agent, or Firm*—Rothwell, Figg, Ernst & Manbeck, P.C.

(57) ABSTRACT

The present invention relates to a process of reducing sulfur- or nitrogen-containing compounds and also producing oxygenates, which can be used as an excellent octane booster in the reformulated gasoline and as a cetane booster for the future oxygenated diesel in a one-pot reaction.

19 Claims, 1 Drawing Sheet

PROCESS FOR THE REDUCTION OF SULFUR, NITROGEN AND THE PRODUCTION OF USEFUL OXYGENATES FROM HYDROCARBON MATERIALS VIA ONE-POT SELECTIVE OXIDATION

CROSS REFERENCE TO RELATED APPLICATIONS

This application claims benefit of U.S. provisional application No. 60/851,052 filed on Oct. 12, 2006, and claims priority from Korean patent application No. 10-2007-56781 filed on Jun. 11, 2007, Korean patent application No. 10-2007-0062496 filed on Jun. 25, 2007 and Korean patent application No. 10-2007-78542 filed on Aug. 6, 2007, all of which are incorporated herein by reference in their entireties for all purposes.

TECHNICAL FIELD

The present invention relates to a process for reducing sulfur- or nitrogen-containing compounds and also producing oxygenates which can be used as an excellent octane booster in the reformulated gasoline and as a cetane booster for the future oxygenated diesel in a one-pot reaction.

RELATED PRIOR ART

Hydrocarbon substrate (e.g. petroleum) contains elemental sulfur and organic aliphatic sulfur compounds such as thiols, sulfides and disulfides, which are generally labile and easily removed by a thermal treatment and other conventional hydrotreating processes.

The conventional hydrodesulfurization (referred to as 'HDS' hereinafter) process technology has been remarkably advanced through the fierce worldwide competition among petroleum refiners as well as academic endeavors, and became a key pivotal process for the petroleum refineries for removing sulfur to meet the stringent air pollution control regulation acted by European countries, the United States and Japan.

Especially, spearheaded by EU countries, the near zero sulfur level (10 ppm S) in the transportation fuels, in particular gasoline, has already been targeted in some European countries. In order to meet the above objective, it is required to develop the deep and/or super deep desulfurization technology. As shown below, a dramatic shift to super clean fuel also occurred in the sulfur regulation for the transportation fuel in South Korea as well.

TABLE 1

| Year | 2006 | 2008 | 2010 |
|---|---|---|---|
| Gasoline, ppm S | 130 | 50 | 10 |
| Diesel oil, ppm S | 430 | 30 | 10 |

However, there are also other forms of organic sulfur like a series of thiophenes and their condensed derivatives, which become increasingly difficult to remove from the hydrocarbon fraction in petroleum.

Among the condensed thiophene derivatives, generally benzothiophenes present in gasoline and the more condensed sulfur compounds, e.g. dibenzothiophene, 4-methyldibenzothiophene, and in particular 4,6-dimethyldibenzothiophene, are found in diesel fuel, the HDS middle distillates, heavier fractions, and residual bottoms of petroleum crudes. Dibenzothiophene and its alkyl derivatives are called as a 'refractory' sulfur compound simply because they are thermally stable at the elevated temperature (650° C.), and are also very difficult to remove by the conventional refinery processes such as the HDS process.

There have been many reports on experimental HDS catalysts that can meet the above objective. However, the HDS process conditions required for these processes are so severe that the essential hydrocarbon components such as olefins, paraffin and aromatics including multi-ring compounds are excessively hydrogenated by consuming an enormous amount of expensive hydrogen. Besides, the resulting HDS product loses a substantial volume by forming the gas products and excessively hydrogenated products. They become no longer a viable transportation fuel due to the significant loss of octane number (for gasoline) or cetane number (for diesel). Consequently, an additional processes, e.g., cracking reaction and blending procedure with special oxygenates should be performed to restore the desired physical and chemical properties such as octane number in the case of gasoline and to meet the oxygen content required by the reformulated gasoline and the future oxygenated diesel, respectively.

DETAILED DESCRIPTION

To overcome the aforementioned problems of the conventional HDS technology, the present invention aims to provide a process for removing the refractory sulfur compounds or at least selectively oxidizing the sulfur compounds, in particular refractory sulfur compounds such as dibenzothiophene and 4,6-dimethyldibenzothiophene, into sulfoxide and sulfone, and the N-moieties into N-oxide and oxime, etc., which are relatively easier to remove.

The process herein also allows to a further oxidation of benzylic and/or allylic compounds contained in the hydrocarbon substrates to form alcohols, ketones, which can be used as an excellent octane booster in the reformulated gasoline and as a cetane booster for the future oxygenated diesel in a controlled oxidation reaction.

According to an aspect of the present invention, there is provided a one-pot process for reducing a sulfur- or a nitrogen-containing compound and producing an oxygenate in a hydrocarbon substrate, which comprises the steps of (a) placing an MC-type homogeneous catalyst in a reactor; (b) adding the hydrocarbon substrate in the reactor; and (c) introducing an oxidant into the reactor.

According to another aspect of the present invention, there is provided a one-pot process for reducing a sulfur- or a nitrogen-containing compound and producing an oxygenate in a hydrocarbon substrate, which comprises (a) converting the sulfur- or the nitrogen-containing compound in the hydrocarbon substrate into a sulfur- or a nitrogen-containing precursor, respectively, and also converting a benzylic or an allylic compound in the hydrocarbon substrate into the oxygenate at the same time via a selective oxidation of the hydrocarbon substrate in the presence of an MC-type homogeneous catalyst and an oxidant; and (b) removing the precursor.

The step (b) is conducted by means of a post-treatment selected among a filtration, a fractionation, a selective adsorption, a solvent extraction, a catalytic destruction, a selective oxidation, a pyrolysis and a combination thereof.

Four functions, i.e. desulfurization, denitrogenation, demetallation and production of oxygenates, may be attained according to various embodiments of the present invention. It is noteworthy that the level of the four functions may be controlled by varying the oxidant/S ratio. This is important in that it is required to modify the oxidation conditions to meet the environmental requirements of near zero content of sulfur and nitrogen and 2.0-2.7% oxygen in the reformulated gasoline as well as future oxygenated diesel.

According to an embodiment of the present invention, there is provided a one-pot process for reducing a sulfur- or a nitrogen-containing compound and producing an oxygenate in a hydrocarbon substrate, which comprises (a) placing an MC-type homogeneous catalyst in a biphasic system; (b) adding the hydrocarbon substrate in the biphasic system; and (c) introducing an oxidant into the biphasic system.

According to another embodiment of the present invention, there is provided a one-pot process for reducing a sulfur- or a nitrogen-containing compound and producing an oxygenate in a hydrocarbon substrate, which comprises (a) converting the sulfur- or the nitrogen-containing compound in the hydrocarbon substrate into a sulfur- or a nitrogen-containing precursor and also converting a benzylic or an allylic compound in the hydrocarbon substrate into the oxygenate at the same time via a selective oxidation of the hydrocarbon substrate in a biphasic system comprising an MC-type homogeneous catalyst and an oxidant; and (b) removing a layer that comprises the a sulfur- or a nitrogen-containing precursor.

Through the selective oxidation, oxygenates that increase an octane number (gasoline) and a cetane number (diesel oil) may be produced, and a nitrogen- or a sulfur-containing compound may also be converted into a nitrogen- or a sulfur-containing precursor that may be separated or removed relatively easily, thus enabling to accomplish the deep and/or super deep desulfurization and denitrogenation.

To effectively remove such sulfur-containing compounds, dealkylation and/or isomerization reactions, i.e., shifting two methyl groups from 4- and 6-positions to other positions, should precede to circumvent the steric effect for the effective sulfur removal reaction to occur. However, the fundamental problem with the conventional HDS technology lies in the fact that 4,6-dimethyldibenzothiophene is the most difficult compound for desulfurization due to the steric hindrance effect posed by two methyl groups in 4- and 6-positions surrounding the sulfur atom in the structure of the substrate. In short, the conventional HDS technology has a critical limitation even with the most advanced version of the HDS catalyst to attain an economically and technically viable process for deep or super deep desulfurization to meet the near zero sulfur target.

Contrary to the steric hindrance effect posed by the structure of 4,6-dimethyldibenzothiophene in the HDS process, the electron releasing function of two methyl groups in 4- and 6-positions in the substrate molecule enhances the electron density on the sulfur atom as shown in Table 2 below, and thus it becomes more susceptible to the electrophilic attack such as the oxidation reaction.

TABLE 2

(Energy & Fuels 2000, 14, 1232-1239)

| Sulfur compound | Formulas | Electron density | K(L/mol × minute) |
| --- | --- | --- | --- |
| Methylphenyl sulfide | Ph—S—CH$_3$ | 5.915 | 0.295 |
| Thiophenol | Ph—SH | 5.902 | 0.270 |
| Diphenyl sulfide | Ph—S—Ph | 5.860 | 0.156 |
| 4,6-DMDBT | (4,6-dimethyldibenzothiophene structure) | 5.760 | 0.0767 |
| 4-MDBT | (4-methyldibenzothiophene structure) | 5.759 | 0.0627 |
| Dibenzothiophene | (dibenzothiophene structure) | 5.758 | 0.0460 |
| 1-Benzothiophene | (benzothiophene structure) | 5.739 | 0.00574 |

TABLE 2-continued (Energy & Fuels 2000, 14, 1232-1239)

| Sulfur compound | Formulas | Electron density | K(L/mol × minute) |
|---|---|---|---|
| 2,5-Dimethylthiophene | | 5.716 | — |
| 2-Methylthiophene | | 5.706 | — |
| Thiophene | | 5.696 | — |

Thus, the reactivity trend of the refractory sulfur compounds, DBT and its alkyl derivatives, toward the selective sulfoxidation process become exactly opposite to that observed in the conventional HDS reaction. The most refractory sulfur compound, 4,6-dimethyldibenzothiophene, which is stable at an elevated temperature (650° C.) and resistant to desulfurization even under the extreme conditions of the HDS process, becomes the easiest substrates for the oxidative desulfurization (referred to as 'ODS' herein after) process as shown below.

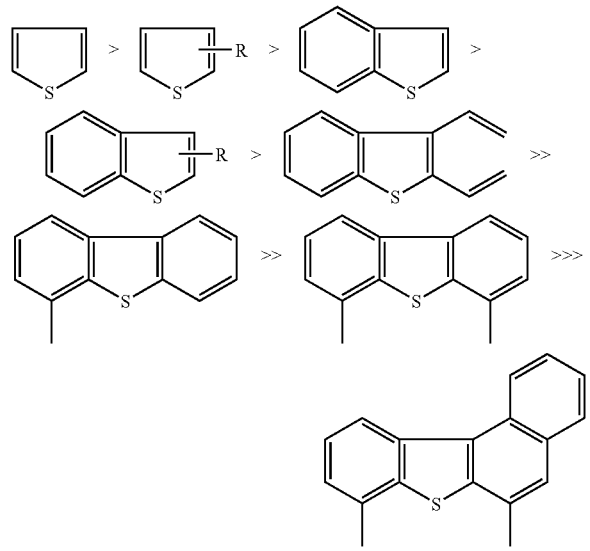

-continued
Reactivity for electrophilic attack: increases ⟶
Electron density on S atom: ⟶

For non-thiophenic sulfur compounds, the electron density on the sulfur atom increases in a direction of diphenyl sulfide<thiophenol<methyl phenyl sulfide, as shown in above. Consequently, the electrophilic attack such as the selective oxidation reaction proceeds in the same trend as that observed in the electron density on the sulfur atom in the oxirane soluble Mo-catalyst. The same chemical principle can also be applied to the selective oxidation of a series of thiophenic derivatives, in particular, refractory dibenzothionphene (DBT), 4-alkylbenzene (4-MDBT) and 4,6-dialkyldibenzothiophene (4,6-DMDBT) in a similar homogeneous catalyst system containing a transition metal ion (see the scheme 1 below).

Further, contrary to the oxygen atom, the sulfur atom can form various compounds by expanding its oxidation state. For example, dibenzothiophene is oxidized to sulfoxide and then to sulfone consecutively in the selective oxidation systems, as illustrated below. In this oxidation process, the physical properties such as a boiling point, a molecular polarity and chemical properties of the oxidized products (i.e., dibenzothiophene sulfoxide and sulfone) are drastically altered.

Utilizing these changes in the physical properties induced by the selective oxidation reaction, the removal of the sulfur impurities could readily be achieved by means of the physical separation techniques such as a fractionation, a solvent extraction and a selective adsorption. Also, the sulfoxide and sulfone products become much more polar and labile, and at the same time, they are also quite liable in extruding SO- and $SO_2$-moieties from the oxidized sulfoxide and sulfones respectively over a variety of catalysts including the chemical destruction catalyst such as base materials.

Scheme 1:
Desulfurization on of 4,6-DMDBT sulfone by means of a base catalyst

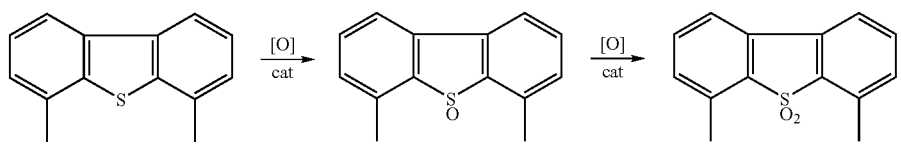

-continued

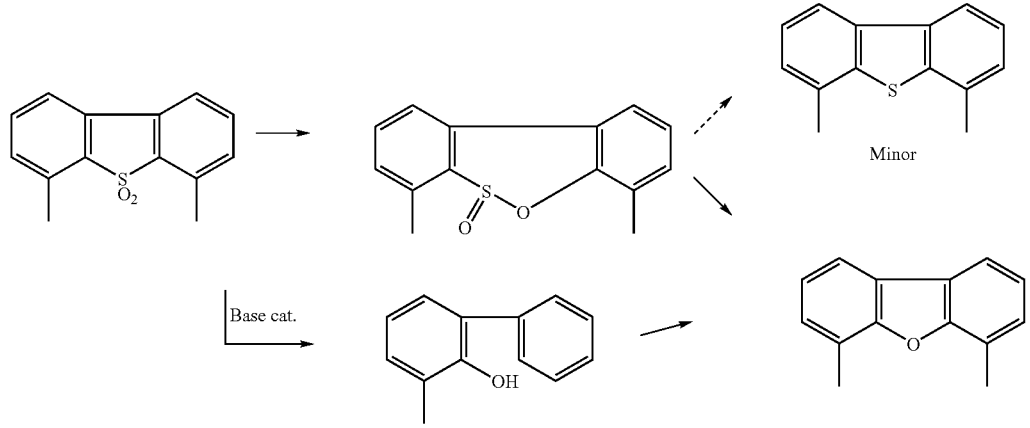

The present invention provides a process for oxidizing the sulfur compounds selectively, in particular refractory sulfur compounds such as dibenzothiophene and 4,6-dimethyldibenzothiophene, to sulfur-containing precursors such as sulfoxide and sulfone, and also oxidizing the N-moieties to nitrogen-containing precursors such as N-oxide and oxime etc. Thus oxidized sulfur- or nitrogen-containing precursors may be easily removed by consecutively conducting various procedures described herein or by conducting a selective oxidation in a biphasic system.

The process herein also allows a further oxidation of the hydrocarbon substrates containing the benzylic and/or allylic carbon to form alcohols and ketones, which can be used as an excellent octane booster in the reformulated gasoline and as a cetane booster for the future oxygenated diesel in a controlled oxidation reaction.

As described above, the removal or separation of sulfur- or nitrogen-containing compounds may be conducted as a separate step or at the same time with the selective oxidation. Therefore, according to another aspect of the present invention, there is provided a process for selectively oxidizing a hydrocarbon substrate, which comprises the oxidation of the hydrocarbon substrate in a biphasic system containing an MC-type homogeneous catalyst and an oxidant, thereby converting a sulfur- or a nitrogen-containing compound in the hydrocarbon substrate into a sulfur- or a nitrogen-containing precursor, respectively, and also converting a benzylic or an allylic compounds into oxygenates at the same time.

According to still another aspect of the present invention, there is provided a process for selectively oxidizing a hydrocarbon substrate, which comprises: (a) converting a sulfur- or a nitrogen-containing compound in the hydrocarbon substrate into a sulfur- or a nitrogen-containing precursor, respectively; and (b) converting a benzylic or an allylic compound into oxygenates at the same time; where the steps (a) and (b) are conducted through a selective oxidation of the hydrocarbon substrate in a biphasic system containing an MC-type homogeneous catalyst and an oxidant.

The sulfur- or nitrogen-containing hydrocarbons and allylic or benzylic hydrocarbons moves into a polar solvent layer such as an aqueous solution or an acetic acid-water layer, and may be removed relatively easily as illustrated below. (i) DBT (or 4,6-DMDBT), (ii) indole and (iii) tetralin are model compounds of (i) a sulfur-containing compound, (ii) a nitrogen-containing compound and (iii) an allylic or benzylic compound, respectively.

Scheme 2

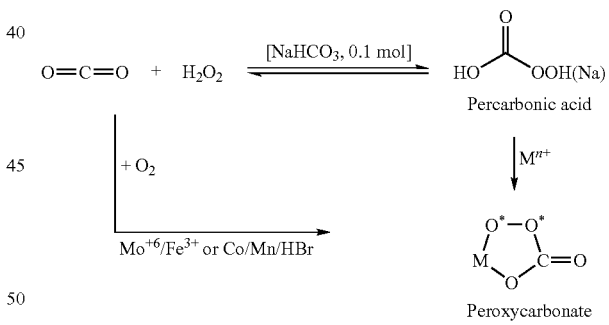

Scheme 3:
Selective extraction in a biphasic system

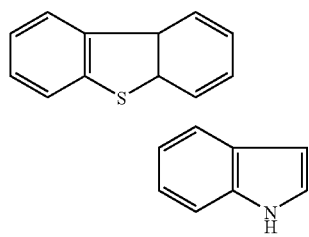

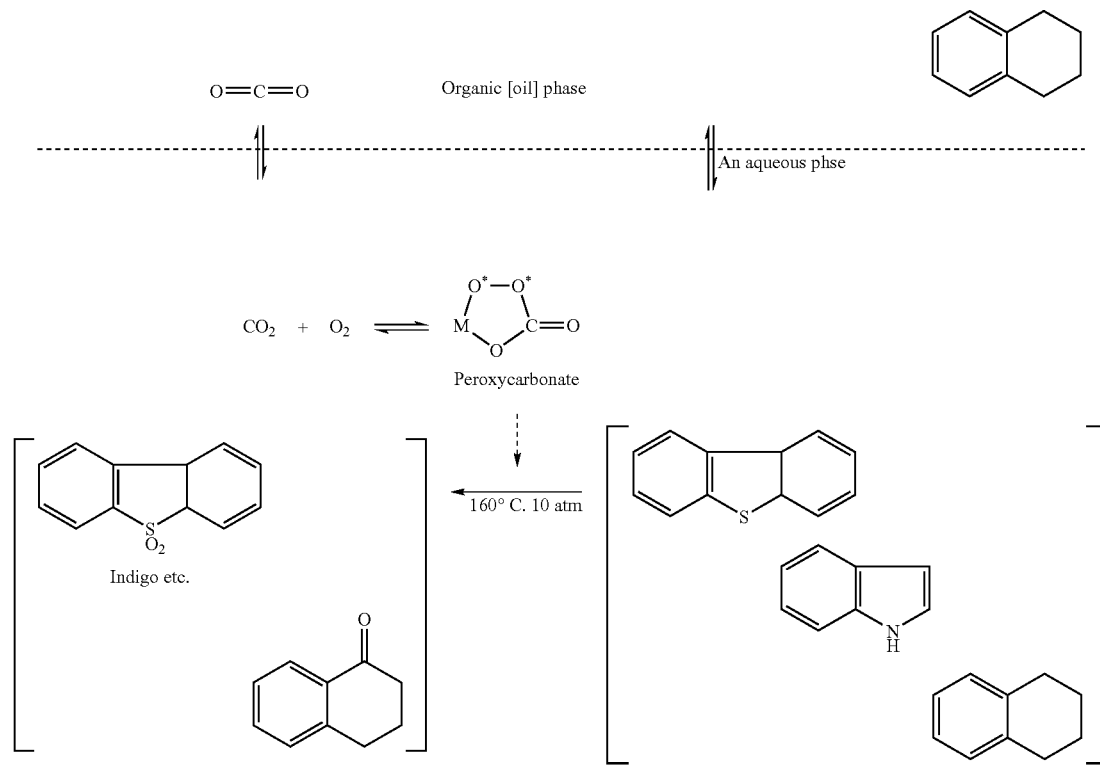

If the nitrogen-containing compound in hydrocarbon substrate exceeds a certain amount, it may hamper the selective oxidation. Thus, a process herein may further comprise the pretreatment step of partially removing a nitrogen-containing compound in the hydrocarbon substrate prior to the selective oxidation. The pretreatment may be conducted by using an absorbent or an excess of an MC-type homogeneous catalyst as because the MC-type homogeneous catalyst may also serve as the absorbent.

As used herein, the term "one-pot process" refers to a process comprising simultaneously or successively adding all reactants into a reactor to have them react together, in which no separation and/or purification of the intermediate state is required before the final product is produced. Sulfur- or nitrogen-containing precursors as defined herein may also be considered as such product as they do not need to be separated and/or removed during the reaction or the process; they are easily separated and/or removed after the reaction is completed.

As used herein, the term "MC-type homogeneous catalyst" refers to a catalyst selected among Co/HBr, Mn/HBr, Co/Mn/HBr and Co/Mn/M'/HBr, where the M' is selected among K, Rb, Cs, Mo, Fe, Zr, Hf, Mn, Ti, Ni, Ru, Nb, Mo, W, Ta, Sb, Re, Rh, Pr, Sm and Ce. Preferably, M' is Ni or Zr.

Various oxidants have been reported for the selective oxidation of hydrocarbons, and examples of such oxidants include organic peroxides such as t-butylhydroperoxide (TBHP), $H_2O_2$/HCOOH, $H_2O_2$/CF$_3$COOH, ethylbenzenehydroperoxide, cumyl hydroperoxide, cyclohexylperoxodicarbonate $(C_6H_{11})_2C_2O_6$), peroxotungstophosphate ($PO_4[W(O)(O_2)_2]_4^{3-}$) and peroxophosphomolybdate; metal peroxides such as perenate (NaReO$_4$), peroxydisulfate (Na$_2$S$_2$O$_8$) and Na$_2$O$_2$; peroxy organic acids such as TBHP, $H_2O_2$, HCOOOH and CH$_3$COOOH; and other peroxides such as ethylbenzene hydroperoxide, cumyl hydroperoxide and cyclohexyl peroxodicarbonate $(C_6H_{11})_2C_2O_6$).

However, as used herein, unless defined otherwise, an "oxidant" or a selective oxidation system of "MC-type homogeneous catalyst-oxidant" refers to an $O_2/CO_2$ mixture, and enables the selective and partial oxidation of hydrocarbon substrate. Preferably, the volumetric ratio of $O_2/CO_2$ is 20-50%/80-50%, more preferably 30-40%/70-60%, and most preferably 35-40%/65-60%.

Further, the $O_2/CO_2$ mixture may comprise 5-30 vol % of helium or argon, whereas nitrogen is preferred to be contained in the amount of less than 20 vol %, more preferably less than 10 vol %, and most preferably less than 5 vol %, because a large amount of nitrogen may lead the oxidation in an undesired direction.

When used in combination with an $O_2/CO_2$ or an $O_2/CO_2$/Ar(N$_2$) oxidant, an MC-type homogeneous catalyst produces intermediate active species such as peroxide, hydroperoxide and peroxocarbonate in situ in a reactor. As illustrated below, these active species function as an oxidant, thus replacing expensive conventional oxidants.

In particular, the production of a poroxocarbonate intermediate is remarkably promoted by the presence of manganese (Mn) component in an MC-type homogeneous catalyst. Therefore, "Co/Mn/HBr" or "Co/Mn/M'/HBr" catalyst is preferred in the present invention among the aforementioned MC-type homogeneous catalysts.

Scheme 4:
A speculative trend in reactivity for oxidation using TBHP in the oxirane blue Mo-solution catalyst

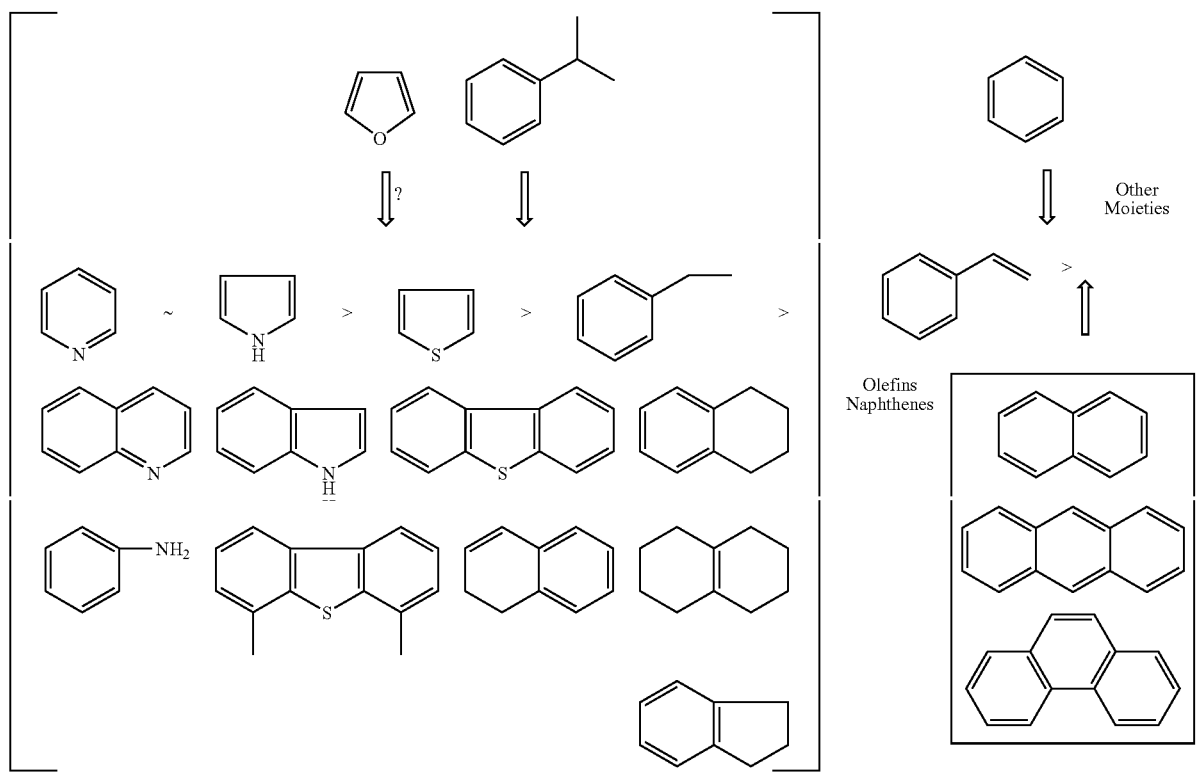

A process herein may remarkably produces a sulfur- or a nitrogen-containing compound, and also produce oxygenates useful in enhancing a cetane number or an octane number. Therefore, as used herein, the term "hydrocarbon substrate" includes any hydrocarbon that comprises a sulfur- or a nitrogen-containing compound to be removed and that needs the production of oxygenates.

Examples of hydrocarbon substrate herein include but are not limited to:

(a) FCC product selected from the group consisting of gasoline, light cycle naphtha (LCN), heavy cycle naphtha (HCN), heavy oil fraction (middle distillate), light cycle oil (LCO), heavy cycle oil (HCO) and clarified oil (CLO);

(b) hydrogenated (HDS or HDN) counterparts of (a) the FCC products;

(c) heavy oil, bunker C oil or atmospheric and vacuum distilled resid bottoms;

(d) asphaltene separated from crude oil;

(e) long crude oil;

(f) tar sand, oil sand;

(g) hydrogenated liquefied coal or H-coal;

(h) chemically cleaned coal that has underwent deashing, desulfurizing and denitrogenating processes; and (i) cokes, graphite or shale oil.

Preferable examples of hydrocarbon substrate herein include without limitation (a) a reformulated gasoline that has underwent desulfurization and denitrogenation through a hydrogenation process, followed by a selective oxidation for increasing the amount of oxygenates; (b) a light cycle oil, a heavy cycle oil, a heavy oil fraction or a mixture thereof that has underwent a hydrogenation; and (c) a reformulated diesel that has underwent desulfurization and denitrogenation through a hydrogenation process, followed by a selective oxidation for increasing the amount of oxygenates.

Among them, a process herein may also be applied to transportation fuel, and even to a gasoline or a diesel that has underwent the conventional HDS process. Consequently, no additional process, e.g., cracking reaction and blending procedure with special oxygenates is not required to restore the desired physical and chemical properties such as octane or cetane number in the case of gasoline and to meet the oxygen content (2.0-2.5 wt % of oxygen) required by the reformulated gasoline and the future oxygenated diesel, respectively.

As used herein, the term "benzylic or allylic compound" includes any benzylic or allylic compound that may be oxidized into oxygenates, which may serve as an octane booster in the reformulated gasoline and a cetane booster for the future oxygenated diesel. Examples of such compound include without limitation tetralin or alkyltetralin derivative; partially hydrogenated naphthalene or naphthene; alkylbenzene derivatives such as xylene, cumene, isopropylbenzene, mesitylene, psuedocuemene and durene; and a mixture thereof.

As used herein, the term "oxygenate" includes any compounds that may increase a cetane number or an octane number of a hydrocarbon substrate herein. Examples of such compound include without limitation alcohols such as α-tetralol and 1-(2-naphthyl)ethanol; ketones such as α-tetralone, 1,4-naphthoquinone and fluorenone; aldehydes such as α-tetralene aldehyde; organic acid esters such as methyloleate, propyl linoleate, butylstearate and aromatic or aliphatic organic acids such as dibutyl meleate, terephthalic acid, 2,6-naphthalenedicarboxylic acid and stearic acid; ethers such as glyme, diglyme, triglyme and tripropylene glycol methyl ether; and a mixture thereof.

As used herein, the term "sulfur-containing compound" refers to any sulfur-containing compound existing in a hydrocarbon substrate herein. Examples of such compound include without limitation dialkyldibenzothiophene (4,6-DMDBT or 2,5-DMDBT), 4-alkyldibenzothiophene (4-MDBT), dibenzothiophene (DBT), alkylbenzothiophene, benzothiophene (BT), dialkylthiophene, thiophene, diphenyl sulfide, thiophenol, methylphenyl sulfide, alkyl disulfide and a mixture thereof.

As used herein, the term "sulfur-containing precursor" refers to any oxygen-containing compounds, into which a sulfur-containing compound herein is oxidized. Examples of such compound include without limitation sulfoxides or sulfones of a sulfur-containing compound herein.

As used herein, the term "nitrogen-containing compound" refers to any nitrogen-containing compounds existing in a hydrocarbon substrate herein. Examples of such compound include without limitation pyridine, quinoline, pyrrole, indole, carbazole, and alkyl derivative thereof, aromatic and aliphatic amines and a mixture thereof.

As used herein, the term "nitrogen-containing precursor" refers to any oxygen-containing compounds, into which a nitrogen-containing compound herein is oxidized. Examples of such compound include without limitation N-oxides, oximes, nitrobenzenes, nitrosobenzenes and indigos of a nitrogen-containing compound herein.

As used herein, the term "biphasic system" refers to any nonpolar or polar system. Examples of such system include without limitation oil/acetonitrile, oil/DMF, oil/acetic acid, oil/pyrrolidone, oil/NaOH aqueous solution, oil/NaHCO$_3$ aqueous solution, oil/Na$_2$CO$_3$ aqueous solution, oil/acetic acid-water mixture, oil/t-BuOH and oil/MeOH.

For such a biphasic system, an "oxidant" or an "oxidation system of homogeneous catalyst-oxidant" may be selected among O$_2$ (10-50%)-CO$_2$/heteropolyacid, O$_2$ (10-50%)-CO$_2$/Mo$^{6+}$ (blue oxirane catalyst solution), O$_2$ (10-50%)-CO$_2$/Mo$^{6+}$—M$^{n+}$ catalyst solution (M=Fe, Co, u, Cu, Zr, Hf, Ni, Zn), hydroperoxide/heteropolyacid, hydrotalcite and hydrotalcite-like materials.

In particular, for a biphasic system of an MC-type catalyst, an oxidant is preferred to be selected among peroxy organic acid such as an O$_2$/CO$_2$ mixture, TBHP, H$_2$O$_2$, HCOOOH and CH$_3$COOOH; or ethylbenzene hydroperoxide, cumylhydroperoxide, cyclohexyl peroxodicarbonate (C$_6$H$_{11}$)$_2$C$_2$O$_6$). Most preferably, an oxidant in a biphasic system of an MC-type catalyst is selected among an O$_2$/CO$_2$ mixture, H$_2$O$_2$, TBHP, HCOOOH, CH$_3$COOOH, and most preferably the oxidant is an O$_2$/CO$_2$ mixture.

A selective oxidation is preferred to be conducted at 1-30 atm, more preferably at 5-20 atm and the most preferably at 10-15 atm. When the reaction pressure is outside the aforementioned ranges, the reaction may not proceed completely or a safety issue may occur. The oxidation temperature is preferably within the range of 80-210° C., more preferably between 130-190° C. and the most preferably between 140-180° C. When the temperature is outside the ranges, oxidation may proceed incompletely or excessively.

Sulfur- or nitrogen-containing compounds may be removed by means of filtration, fractionation, selective adsorption, solvent extraction, catalytic destruction, selective oxidation, pyrolysis and a combination thereof.

The filtration may be conducted by removing or separating sulfur- or nitrogen-containing precursors, which are produced during the selective oxidation and precipitated in a polar solvent layer by a filtration or a centrifugation.

The selective adsorption may be conducted by using one or more adsorbent selected among activated carbon fiber, carbon nanotube, carbon molecular sieve; M/activated carbon fiber, M/carbon nanotube, M/carbon molecular sieve (M=Pd, Zn, Cu, Ni, Fe, Mn, Ti, Mg, Sr, Ba, Na, K); mesoporous alumina, silica gel, zeolite; metal-activated mesoporous alumina, metal-activated silica gel, metal-activated zeolite; M/Al$_2$O$_3$, SiO$_2$, MCM-41 (M=Y, La, Ni, Mo, Cr, W, V, Co, Cu), Perovskite, Y$^{3+}$-stabilized metal oxide; ZrO$_2$, CeO$_2$—ZrO$_2$ and PrO$_2$—ZrO$_2$; solid solutions such as MgO—MgAl$_2$O$_4$, MgAl$_2$O$_4$.xMgO and MgAl$_2$O$_4$.yAl$_2$O$_3$; Cs/ZSM-5, Cs/SiO$_2$, Ba/MCM-41, Zn—Al double layered hydroxide (DLH), hydrotalcite, AlGaPON, ZrGaPON, Mg$_{0.819}$Ga$_{0.181}$(OH)$_2$(CO$_3$).

The solvent extraction may be conducted by using one or more solvent selected from N,N'-dimethyl formamide (DMF), CH$_3$CN, DMSO, MeOH, t-BuOH, methyl ethyl ketone (MEK), CH$_3$COOH and CX$_3$COOH, dimethylpyrrolidone, dioxane, sulfolane, alkaline metal and sodium carbonate (NaHCO$_3$, Na$_2$CO$_3$) aqueous solution.

The catalytic destruction may be conducted in the presence of one or more base catalyst selected from t-BuONa, NaOH, NaOH—KOH, CH$_3$CO$_2$Na, Li$_2$CO$_3$—NaCO$_3$—K$_2$CO$_3$ eutectic mixture, Raney Ni, Raney Fe, Na/K, Na/Al$_2$O$_3$, K/Al$_2$O$_3$, Li/MgO, Cs/SiO$_2$, MgFe$_2$O$_4$, [Ni(COD)$_2$Bipy], commercial HDS catalyst, commercial HDN catalyst, hydrotalcite, Ce/V/MgO.MgAl$_2$O$_4$, MgO.MgAl$_2$O$_4$ solid solution and Zn—Al double-layered hydroxides.

The pyrolysis may be applied to dihydronaphthalene, tetralin, decaline, hydrogenated LCN, LCO and HCO, and may be conducted in the presence of one or more base catalyst selected from the H-donor solvent and/or MgO.MgAl$_2$O$_4$, xAl$_2$O$_3$.yMgAl$_2$O$_4$ solid solution, Cs/ZSM-5, Ba/MCM-41, Cs/SiO$_2$, Zn—Al double-layered hydroxide, hydrotalcite and hydrotalcite-like materials, Li/MgO, Li/MgO—CaO, Na/Al$_2$O$_3$, K/Al$_2$O$_3$, AlGaPON, ZrGaPON and Mg$_{1-x}$Ga$_x$(OH)$_2$CO$_3$.

Various kinds of wasted catalysts such as a spent FCC catalyst, a spent RFCC catalyst, a zeolite (ZSM-5, MCM-41, etc.), a commercial HDS catalyst and a commercial HDN catalyst may be recycled and used as the MgO.MgAl$_2$O$_4$, the xAl$_2$O$_3$.yMgAl$_2$O$_4$ solid solution, the Ce/V/MgO.MgAl$_2$O$_4$, (commercial DeSOx catalyst), the Cs/ZSM-5, the Na/Al$_2$O$_3$, the K/Al$_2$O$_3$, the Cs/SiO$_2$, the Ba/MCM-41, NaOH—KOH, NaOH, CVD Fe/Mo/DBH, FCC catalyst.

In the present invention, the desulfurization is preferred to be conducted to such a level that sulfur-containing compounds may be removed less than 20 ppm, more preferably less than 10 ppm, the most preferably less than 5 ppm, and ultimately 0 ppm.

Preferably, the desulfurization is also conducted to such a level that nitrogen-containing compounds may be removed less than 10 ppm, preferably less than 5 ppm, most preferably less than 2.5 ppm, and ultimately 0 ppm.

The extent of oxidizing the benzylic and allylic hydrocarbons can be determined by the oxygen content stipulated for the current and future transportation fuels, e.g., the requirements for the octane number of the reformulated gasoline and the cetane number for the future oxygenated diesel, the level of the benzylic hydrocarbon existing in the feed substrate and other environmental regulations on the oxygen content.

EXAMPLES

Figure 1:
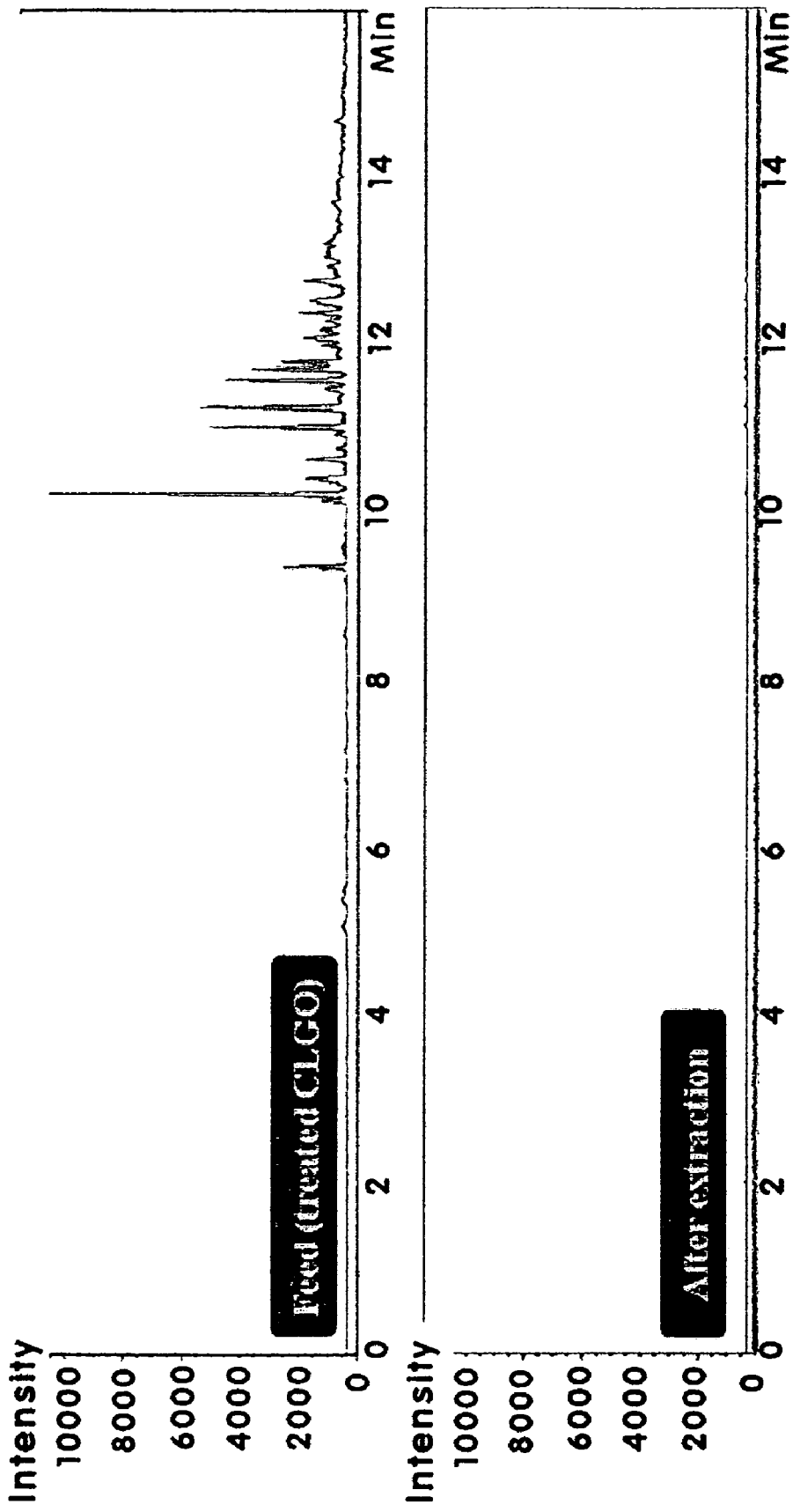
FIG. 1 is a GC-PFPD graph showing the results of the selective oxidation of CLGO as described in Example 4.

The present invention is described more specifically by the following Examples. Examples herein are meant to illustrate the present invention only, but they should not be construed as limiting the scope of the claimed invention.

Example 1

Selective Oxidation of Indole (N-Compound)

Nitrogen-containing compounds present in petroleum may be divided into 3 classes: (i) aliphatic and aromatic amines, (ii) pyrrole-type acidic N-compound and (iii) pyridine-type basic N-compound. Among them, indole was used in this Example.

Selective oxidation was conducted by using indole (99%, Aldrich) as a nitrogen model compound and acetic acid (glacial, 99.8%, Aldrich) as a solvent in the presence of Co/Mn/HBr catalyst, which was prepared using Co(OAc)$_2$.4H$_2$O (98%, Aldrich), Mn(OAc)$_2$.4H$_2$O (99%, Aldrich) and HBr (48%, Aldrich) in a Ti-autoclave for 2 hours under the conditions of 10 atm, 150° C. and 350 rpm, while introducing O$_2$/CO$_2$ (30%/70%).

Analysis of products using GC-MS (Agilent 5973I) and GC-FID (Agilent 6890N) shows that nitrogen-containing substrate was completely oxidized and undetectable at one hour time point of the experiment.

Example 2

Selective Oxidation of Tetralin (Benzylic Compound)

Examples of benzylic hydrocarbon present in petroleum resids, in particular hydrotreated petroleum resids are alkyl derivative (n-, iso, tertiary) of benzene and naphthalene, partially hydrogenated condensed multi-ring compound, tetralin, naphthenes, octalin, dihydronaphthalene, dihydroindole, cyclohexylbenzene, alkyl derivative (n-, iso-tertiary) thereof, naphthocycloparaffin and alkyl derivative (n-, iso, tertiary) thereof.

Among the oxygenates known as an excellent cetane or octane booster as shown below, 1,4-naphthoquinone, which is easily produced according to the present invention, has twice more amount of oxygen than α-tetralone, thus being superior in enhancing cetane or octane number. Further, the compound also remarkably reduces the production of particulate matters (PM), NOx and SOx.

Formulas: Oxygenates known as an excellent cetane or octane booster

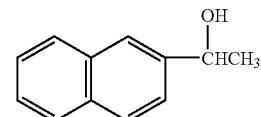

1-(2-Haphthyl)-ethanol
Cetane: +17.6

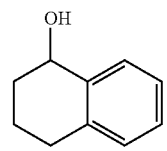

Alpha-Tetralol
Cetane: +12.8

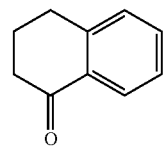

Alpha-Tetralone
Cetane: +15.1

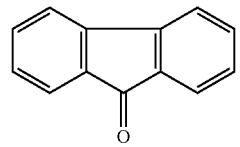

Fluorenone
Cetane: +14.1

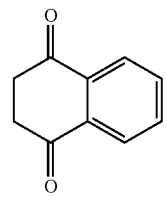

1,4-Haphthoquinone

Among the aforementioned benzylic hydrocarbon, tetralin was used as a model compound in this Example. A liquid-phase oxidation of tetralin was conducted in a Ti-autoclave in the presence of various MC-type catalysts such as Co/HBr, Mn/HBr, Co/Mn/HBr, Ni/Co/Mn/HBr and Zr/Co/Mn/HBr by varying the oxidation conditions as described below.

Analysis of oxygenates and other side-products shows the that useful oxygenates, particularly α-tetralone, 1,4-naphthoquinone and phthalic anhydride, were produced in a high yield. In particular, 1,4-naphthoquinone, which was successfully produced via selective oxidation for the first time, is expected to serve as a cetane or octane booster due to a high oxygen content (20 wt %) and cetane number of about 60.

Scheme 5

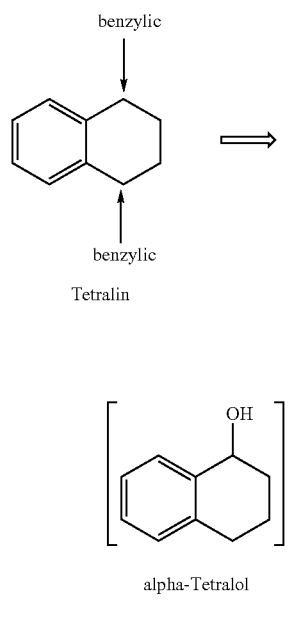

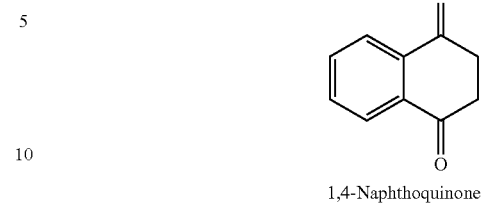

1,4-Naphthoquinone

Conditions of Selective Oxidation

Selective oxidation was conducted as set forth in Table 3 by using tetralin (99%, Aldrich) and acetic acid (glacial, 99.8%, Aldrich) as a benzylic hydrocarbon model compound and a solvent, respectively in the presence of a catalyst prepared by using Co(OAc)$_2$.4H$_2$O (98%, Aldrich), Mn(OAc)$_2$.4H$_2$O (99%, Aldrich), HBr (48%, Aldrich), Ni(OAc)$_2$.4H$_2$O (98%, Aldrich) and Zr acetate solution (~15% Zr, Aldrich) in a Ti-autoclave under the conditions of 10 atm, 150° C. and 350 rpm while introducing O$_2$/CO$_2$ (26-40%/60-74%). Products were analyzed with GC-MS (Agilent 59731) and GC-FID (Agilent 6890N).

TABLE 3

| Ex. | Total wt. | Tetralin (mmol) | Co (mmol) | Mn (mmol) | Br (mmol) | Ni(Zr) (mmol) | Temp. | Press. | Time | Oxidant (O$_2$/CO$_2$) |
|---|---|---|---|---|---|---|---|---|---|---|
| 2-0 | 120 g | 10 | 0.1 | — | 0.3 | — | 150° C. | 10 atm | 3 hr | 30/70 |
| 2-1 | 120 g | 10 | 0.1 | 0.5 | 0.3 | | 150° C. | 10 atm | 3 hr | 30/70 |
| 2-2 | 120 g | 10 | 0.1 | 0.5 | 0.3 | 0.07 | 150° C. | 10 atm | 3 hr | 30/70 |
| 2-3 | 120 g | 10 | 0.1 | 0.5 | 0.3 | 0.07 | 150° C. | 10 atm | 3 hr | 30/70 |
| 2-4 | 120 g | 10 | 0.1 | 0.5 | 0.3 | — | 150° C. | 5 atm | 3 hr | 30/70 |
| 2-1 | 120 g | 10 | 0.1 | 0.5 | 0.3 | — | 150° C. | 10 atm | 3 hr | 30/70 |
| 2-5 | 120 g | 10 | 0.1 | 0.5 | 0.3 | — | 150° C. | 15 atm | 3 hr | 30/70 |
| C2-1* | 120 g | 10 | 0.1 | 0.5 | 0.3 | — | 150° C. | 30 atm | 3 hr | 30/70 |
| C2-2* | 120 g | 10 | 0.1 | 0.5 | 0.3 | — | 110° C. | 10 atm | 3 hr | 30/70 |
| 2-6 | 120 g | 10 | 0.1 | 0.5 | 0.3 | — | 130° C. | 10 atm | 3 hr | 30/70 |
| 2-1 | 120 g | 10 | 0.1 | 0.5 | 0.3 | — | 150° C. | 10 atm | 3 hr | 30/70 |
| 2-7 | 120 g | 10 | 0.1 | 0.5 | 0.3 | — | 190° C. | 10 atm | 3 hr | 30/70 |
| 2-8 | 120 g | 10 | 0.1 | 0.5 | 0.3 | — | 150° C. | 10 atm | 0.5 hr | 30/70 |
| 2-9 | 120 g | 10 | 0.1 | 0.5 | 0.3 | — | 150° C. | 10 atm | 1 hr | 30/70 |
| 2-1 | 120 g | 10 | 0.1 | 0.5 | 0.3 | — | 150° C. | 10 atm | 3 hr | 30/70 |
| 2-10 | 120 g | 10 | 0.1 | 0.5 | 0.3 | — | 150° C. | 10 atm | 4 hr | 30/70 |
| 2-11 | 120 g | 10 | 0.1 | 0.5 | 0.3 | — | 150° C. | 10 atm | 5 hr | 30/70 |
| 2-12 | 120 g | 10 | 0.1 | 0.5 | 0.3 | — | 150° C. | 10 atm | 3 hr | 26/74 |
| 2-13 | 120 g | 10 | 0.1 | 0.5 | 0.3 | — | 150° C. | 10 atm | 3 hr | 29/71 |
| 2-1 | 120 g | 10 | 0.1 | 0.5 | 0.3 | — | 150° C. | 10 atm | 3 hr | 30/70 |
| 2-14 | 120 g | 10 | 0.1 | 0.5 | 0.3 | — | 150° C. | 10 atm | 3 hr | 35/65 |
| 2-15 | 120 g | 10 | 0.1 | 0.5 | 0.3 | — | 150° C. | 10 atm | 3 hr | 40/60 |
| 2-16 | 120 g | 10 | 0.1 | 0.5 | 0.3 | 0.07 | 150° C. | 10 atm | 3 hr | 35/65 |
| C2-3* | 120 g | 10 | 0.1 | 0.5 | 0.3 | 0.07 | 150° C. | 10 atm | 3 hr | 20/74 |
| C2-4* | 120 g | 10 | 0.1 | 0.5 | 0.3 | 0.07 | 150° C. | 10 atm | 3 hr | Air |

*Comparative Examples

Results of Selective Oxidation

As shown in Table 4, α-tetralone was produced as a main product. It was ascertained that controlled oxidation conditions easily converts α-acetoxytetralin to α-tetralol and increases the yields of 1,4-aphthoquinone and phthalic anhydride. Further, Co/Mn/HBr/Ni (Zr) catalyst showed a higher conversion and selectivity than Co/Mn/HBr. The production of by-products such as naphthalene and dihydronaphthalene was minimized by adjusting the conditions and catalyst composition.

Meanwhile, the promoting activity of $CO_2$ was not observed in the presence of Co/HBr catalyst without Mn component, which ascertains that the $O_2/CO_2$ oxidant is activated on Mn site, thus forming 'a peroxocarbonate intermediate active species'.

Example 3

Selective Oxidation of Synthetic Model Compounds Feeds (1) Preparation of Synthetic Model Compounds Feeds Examples of hydrocarbon substrate appropriate for this experiment are FCC products such as LCN (41-129° C.), HCN (129-204° C.), distillate (204-338° C.), LCO (329-385° C.), CLO (clarified oil) (360-650° C.) and particularly transportation fuel (e.g., gasoline and diesel).

Synthetic model compounds feeds similar to the aforementioned hydrocarbon substrate are prepared as in Table 5 by using sulfur component, nitrogen component and benzylic hydrocarbon, specifically n-decane (99%, Aldrich), n-hexadecane (99%, Aldrich), DBT (dibenzothiophene, 98%, Aldrich), 4,6-DMDBT (4,6-dimethyl dibenzothiophene, 97%, Aldrich), tetralin (99%, Aldrich) and indole (99%, Aldrich).

TABLE 4

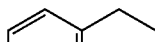

| Ex. (%) | | | | | | |
|---|---|---|---|---|---|---|
| 2-0 | 39 | 15 | 10 | 31 | 4 | 0 |
| 2-1 | 31 | 11 | 12 | 39 | 6 | 0 |
| 2-2 | 22 | 6 | 10 | 52 | 8 | 0 |
| 2-3 | 20 | 8 | 11 | 51 | 7 | 0 |
| 2-4 | 66 | 2 | 4 | 17 | 2 | 5 |
| 2-1 | 31 | 11 | 12 | 39 | 6 | 0 |
| 2-5 | 26 | 13 | 25 | 32 | 1 | 0 |
| C*2-1 | 18 | 37 | 26 | 15 | 0 | 0 |
| C*2-2 | 89 | 1 | 1 | 0 | 0 | 8 |
| 2-6 | 36 | 7 | 10 | 33 | 7 | 3 |
| 2-1 | 31 | 11 | 12 | 39 | 6 | 0 |
| 2-7 | 12 | 19 | 29 | 35 | 1 | 0 |
| 2-8 | 69 | 1 | 3 | 6 | 0 | 19 |
| 2-9 | 56 | 4 | 5 | 19 | 2 | 12 |
| 2-1 | 31 | 11 | 12 | 39 | 6 | 0 |
| 2-10 | 26 | 14 | 13 | 40 | 5 | 0 |
| 2-11 | 21 | 19 | 17 | 37 | 4 | 0 |
| 2-12 | 73 | 7 | 5 | 10 | 3 | 0 |
| 2-13 | 61 | 6 | 7 | 19 | 5 | 0 |
| 2-1 | 31 | 11 | 12 | 39 | 6 | 0 |
| 2-14 | 12 | 12 | 18 | 50 | 5 | 0 |
| 2-15 | 15 | 13 | 18 | 48 | 4 | 0 |
| 2-16 | 9 | 8 | 19 | 56 | 5 | 0 |
| C*2-3 | 62 | 17 | 11 | 8 | 0 | 0 |
| C*2-4 | 78 | 8 | 6 | 5 | 0 | 1 |

*Comparative Examples

TABLE 5

| Total | n-Decane | n-Hexadecane | DBT (ppm/mmol) | 4,6-DMDBT (ppm/mmol) | Tetralin (ppm/mmol) | Indole (ppm/mmol) |
|---|---|---|---|---|---|---|
| 100 g | 48.975 g | 48.975 g | 0.500 g (5,000/2.69) | 0.500 g (5,000/2.28) | 1.000 g (10,000/7.49) | 0.050 g (500/0.42) |

(2) Selective Oxidation Using Co/Mn/HBr or Ni—Co/Mn/HBr Catalyst

Liquid-phase oxidation was conducted in a 200 mL Ti-autoclave in the presence of Co/Mn/HBr or Ni—Co/Mn/HBr catalyst for 3 hours at 10 atm, 150° C. and 350 rpm while introducing $O_2/CO_2$ (26-40%/60-74%) or $O_2/(CO_2, Ar, N_2$ or premixed) gas.

Acetic acid (glacial, 99.8%, Aldrich) was used as a solvent. A catalyst was prepared by using $Co(OAc)_2 \cdot 4H_2O$ (98%, Aldrich), $Mn(OAc)_2 \cdot 4H_2O$ (99%, Aldrich), HBr (48%, Aldrich) and $Ni(OAc)_2 \cdot 4H_2O$ (98%, Aldrich).

Products were analyzed by GC-MS (Agilent 59731) and GC-FID, PFPD (Agilent 6890N).

Scheme 7

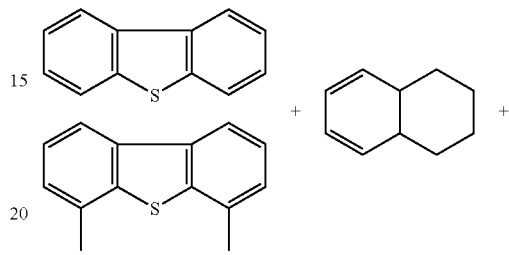

TABLE 6

| Ex. | Total wt. | Model diesel | Solvent | Co (mmol) | Mn (mmol) | Br (mmol) | Ni (mmol) | Oxidant (%) | | | | |
|---|---|---|---|---|---|---|---|---|---|---|---|---|
| | | | | | | | | $O_2$ | $CO_2$ | $N_2$ | Ar | Air |
| 4-1 | 100 g | 90 g | Balance | 0.1 | 0.5 | 0.3 | — | 26 | 74 | — | — | — |
| 4-2 | 100 g | 90 g | Balance | 0.1 | 0.5 | 0.3 | — | 29 | 71 | — | — | — |
| 4-3 | 100 g | 90 g | Balance | 0.1 | 0.5 | 0.3 | — | 30 | 70 | — | — | — |
| 4-4 | 100 g | 90 g | Balance | 0.1 | 0.5 | 0.3 | — | 35 | 65 | | | |
| 4-5 | 100 g | 90 g | Balance | 0.1 | 0.5 | 0.3 | — | 40 | 60 | — | — | — |
| 4-6 | 100 g | 90 g | Balance | 0.1 | 0.5 | 0.3 | 0.07 | 40 | 60 | — | — | — |
| 4-7 | 100 g | 90 g | Balance | 0.1 | 0.5 | 0.3 | — | 30 | — | — | 70 | — |
| C*4-1 | 100 g | 90 g | Balance | 0.1 | 0.5 | 0.3 | — | — | — | — | — | 100 |
| C*4-2 | 100 g | 90 g | Balance | 0.1 | 0.5 | 0.3 | — | 26 | — | 74 | — | — |
| C*4-3 | 100 g | 90 g | Balance | 0.1 | 0.5 | 0.3 | 0.07 | 26 | — | 74 | — | — |

*Comparative Examples (3) Results of Selective Oxidation

Oil fractions from the products produced via selective oxidation were analyzed, and the results are presented in Table 7. Sulfur or nitrogen compounds and benzylic hydrocarbons were ascertained to penetrate the solvent layer. Other results ascertained are presented in Schemes 6 and 7 below.

Scheme 7

DBT $\xrightarrow[\text{HOAc}]{\text{Co/Mn/HBr}}$ DBTO (sufoxide) + DBTO2(sulfone)

4,6-DMDBT ⟶ 4,6-DMDBTO + 4,6-DMDBTO2

Indole ⟶ No unreacted substrate detected (Completely oxidized)

Tetralin ⟶ α-Tetralone n-Decane, n-Hexadecane ⟶ Partially oxidzed/cracked products -continued

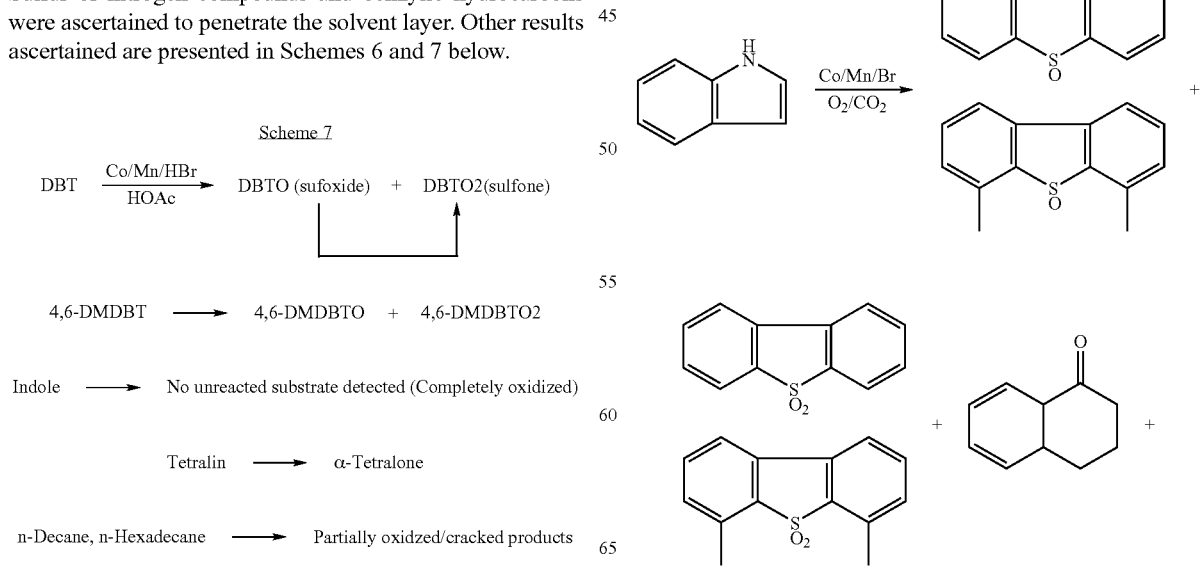

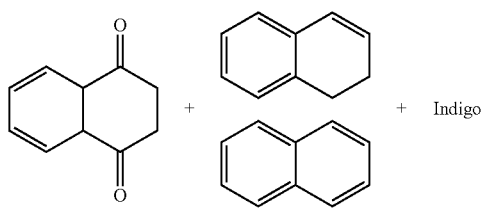

As shown in Table 7, the conversion and the selectivity were superior when the partial pressure of oxygen is within 35-40% (in the presence of $CO_2$). These results show that S- or N-compounds and allylic or benzylic hydrocarbon may be oxidized via a one-pot reaction, which allows achieving super deep desulfurization and denitrogenation and the production of useful oxygenates at the same time.

In this respect, a process herein is deemed to provide an eco-friendly future process for refining petroleum.

Example 4

Selective Oxidation of Treated CLGO (1) Treatment of Selective Oxidation

Liquid-phase oxidation was conducted in 200 mL Ti-autoclave in the presence of Co/Mn/HBr catalyst by using treated CLGO (coker light gas oil) containing 820 ppm of sulfur compounds at 10 atm, 150° C. and 350 rpm for 3 hours while introducing an $O_2/CO_2$ (35%/65%) mixture at a rate of 400 cc/min.

In details, the composition of the treated CLGO is provided in Table 9, and acetic acid (glacial, 99.8%, Aldrich) was used as a solvent. The catalyst was prepared by using $Co(OAc)_2 \cdot 4H_2O$ (98%, Aldrich), $Mn(OAc)_2 \cdot 4H_2O$ (99%, Aldrich) and HBr (48%, Aldrich).

TABLE 8

| Ex. | Total wt. | Treated CLGO | Solvent | Co (mmol) | Mn (mmol) | Br (mmol) | Oxidant (%) $O_2$ | $CO_2$ |
|---|---|---|---|---|---|---|---|---|
| 4-1 | 100 g | 90 g | Balance | 0.1 | 0.5 | 0.3 | 35 | 65 |

TABLE 7

| Ex. (%) | DBT (100%) | | | 4,6-DMDBT (100%) | | |
|---|---|---|---|---|---|---|
| | DBT | DBT-O | DBT-$O_2$ | 4,6-DMDBT | 4,6-DMDBT-O | 4,6-DMDBT-$O_2$ |
| 4-1 | 34 | 33 | 30 | 28 | 43 | 33 |
| 4-2 | 32 | 34 | 31 | 25 | 45 | 34 |
| 4-3 | 24 | 37 | 35 | 7 | 36 | 54 |
| 4-4 | 9 | 29 | 59 | 0 | 34 | 62 |
| 4-5 | 7 | 23 | 64 | 0 | 33 | 64 |
| 4-6 | 6 | 23 | 67 | 0 | 35 | 64 |
| 4-7 | 27 | 36 | 38 | 6 | 38 | 52 |
| C*4-1 | 88 | 8 | 1 | 72 | 15 | 7 |
| C*4-2 | 41 | 44 | 9 | 35 | 41 | 22 |
| C*4-3 | 40 | 45 | 12 | 32 | 45 | 21 |

| Ex. (%) | Tetralin (100%) | | | | | Indole (100%) | |
|---|---|---|---|---|---|---|---|
| | | | | | | Indole | Indigo |
| 4-1 | 48 | 5 | 45 | Large | | 0 | — |
| 4-2 | 45 | 6 | 48 | amount in | | 0 | — |
| 4-3 | 34 | 4 | 57 | solvent layer | | 0 | — |
| 4-4 | 21 | 5 | 72 | | | 0 | — |
| 4-5 | 19 | 3 | 74 | | | 0 | — |
| 4-6 | 18 | 4 | 77 | | | 0 | — |
| 4-7 | 31 | 5 | 56 | | | 0 | — |
| C*4-1 | 86 | 7 | 6 | Small | | 3 | — |
| C*4-2 | 52 | 23 | 21 | amount in | | 0 | — |
| C*4-3 | 53 | 20 | 24 | solvent layer | | 0 | — |

*Comparative Examples

TABLE 9

| Compounds | | Treated CLGO |
|---|---|---|
| Sulfur Species (wt %) | | 0.082 |
| Sulfur Species (ppm) | DBT | 16 |
| | 4-MDBT | 30 |
| | 4,6-DMDBT | 153 |
| | 2,3-DP-4-MT | 335 |
| | 2,3-DMDBT | 70 |
| | 1,2-DMDBT | 65 |
| Aromatic compounds | T-Aromatic (wt %) | 27.7 |
| | P-Aromatic-Di+ (wt %) | 7.1 |
| IBP-EP (° C.) | | 177-382 |
| Total Nitrogen (ppm) | | 334 |

(2) Post-Treatment: Solvent Extraction

Oxidized products obtained in (1) above were treated by using acetic acid. Sulfur compound remaining in the treated products was measured by PFPD (Agilent 6890N). As shown in FIG. 1, sulfur compound was successfully removed (almost 98.9%).

Such sulfur compound as DBT were oxidized into polar compounds such as sulfone and sulfoxide, which are easily removed after moving into a polar solvent (acetic acid). Small amount of acetic acid (boiling point: 117-118° C.) was also easily removed by means of distillation.

(3) Post-Treatment: Selective Adsorption

Oxidized products obtained in (1) above were treated by a commercial activated carbon absorbent at atmospheric pressure and room temperature. Only a small amount of sulfur compounds were analyzed by KS M 2027-2005 method (13 ppm) and an elemental analysis (1.1%). The yield of desulfurization is remarkably higher than that of Comparative Examples below, where absorbent treatment was conducted without oxidation.

(4) Selective Adsorption without Selective Oxidation

Treated CLGO was treated by an absorbent as described in (3) without conducting a selective oxidation. As a result of the KS M 2027-2005 analysis, sulfur component was ascertained to remain at the amount of 208 ppm.

Example 5

Selective Oxidation of HCN (1) Selective Oxidation

Selective oxidation of HCN (heavy cyclic naphtha) containing 0.12% of sulfur component and 45 ppm N component was conducted at 80° C. for 2 hours in the presence of Co/Mn/HBr catalyst by using an $O_2/CO_2$ (26%/74%) oxidant system.

(2) Post-Treatment: Filtration

Oxidized products obtained in (1) above were filtered by using a glass filter and an aspirator under the reduced pressure. After the filtration, sulfur compounds were analyzed to be less than 25 ppm, and no nitrogen-containing compound was detected.

These remarkable results are ascribed to the fact that DBT and indole are oxidized into their corresponding sulfone and indigo, respectively, and precipitated as solid matters, which are easily removed by means of filtration.

(3) Post-Treatment: HDS

Oxidized products obtained in (1) above were hydrogenated in the presence of the conventional HDS catalyst, Ni (6%)-Mo (18%)/$\gamma$-$Al_2O_3$ (M=Ti, Zr, B, P). After the treatment, sulfur compounds were analyzed to be less than 20 ppm, and no nitrogen-containing compound was detected.

These results show that refractory condensed thiophenes existing in resids are preferentially oxidized into their corresponding sulfones, and relatively easily removed, thus achieving super deep desulfurization.

(4) Post-Treatment: Cracking Using FCC Recycled Catalyst

Oxidized products obtained in (1) above underwent hydrocracking and normal cracking by using a spent FCC catalyst loaded with Ni, V and Fe. After the treatment, sulfur compounds were analyzed to be less than 10 ppm, and no nitrogen-containing compound was detected.

These results show that remarkable desulfurization may be achieved by recycling spent catalysts containing a large amount of V, Ni and Fe collected form FCC and RFCC (resid fluid catalytic cracking).

Example 6

Selective Oxidation of CLGO

CLGO (coker light gas oil, boiling point: 162-375° C.) contains 825 ppm of nitrogen compounds and 2.07% of sulfur compounds such as BT (96 ppm), 4-MDBT (520 ppm), 4,6-DMDBT (387 ppm), 2,3-DP-4-MT (457 ppm), 2,3-DMDBT (291 ppm) and 1,2-DMDBT (624 ppm).

CLGO were oxidized in a biphasic system (oil/acetic acid-$H_2O$) by using a Ti-autoclave at 140° C. and 15 atm in the presence of Co/Mn/HBr or M/Co/Mn/HBr (M=Ni, Fe, To, Zr, Jf, Ru, Re, Ce) catalyst while introducing $O_2$ (25%)/$CO_2$ (75%). The biphasic system consists of an oil-phase substrate and an aqueous layer containing acetic acid-$H_2O$ aqueous solution and Co/Mn/HBr catalyst.

Sulfones were produced in a remarkable yield (>94%), and N-oxides were produced in a yield of almost 100%. Further, a significant amount of oxygenates were generated and observed to penetrate into the acetic acid-$H_2O$ aqueous layer.

Example 7

Selective Oxidation of LCO (1) Selective Oxidation Using "MC-TYPE Catalyst" and "$O_2$/$CO_2$ Oxidant"

Selective oxidation was conducted in the same condition as illustrated in Example 6 except that a MC-type homogeneous catalyst and $O_2$ (30%)/$CO_2$ (70%) were used as a catalyst and an oxidant, respectively. Further, the reaction was conducted in 1 liter autoclave (1 L) under the pressure of 15 atm.

(2) Production of S- or N-Containing Precursors and Oxygenates Via Selective Oxidation IR analysis shows that the resulting oxidized products were analyzed to be almost 100% sulfone and contain easily removable N-containing precursors, and that a significant amount of carbonyl compounds were produced.

(3) Post-Treatment: Pyrolysis

An aliquot portion (40 mL) of the product was subjected to pyrolysis in the presence of H-donor solvent at 4,570° C. for 3 hours in a pyrolysis unit. As shown in Table 10, remarkable desulfurization (92-97%) was achieved and no N-containing compound was detected. When naphthalene existed instead of H-donor solvent, desulfurization decreased to 83%.

TABLE 10

| H-donor | | Desulfurization % pyrolysis w/o cat. |
|---|---|---|
| 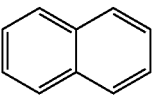 | Naphthalene* | 83 |
| 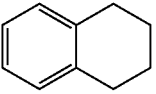 | Tetralin | 97 |
| 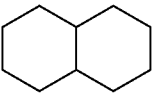 | Decalin | 90 |
| 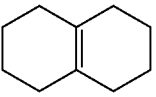 | Octalin | 92 |
| 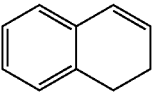 | Dihydronaphthalene | 95 |
| 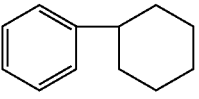 | Cyclohexylbenzene | 94 |

*For comparison (4) Post-Treatment: Pyrolysis in the Presence of Base Catalyst

Another aliquot portion (40 mL) of the oxidized product underwent pyrolysis in a pyrolysis unit at 450° C. for one hour after introducing 5 g of base catalyst such as hydrotalcite, Na/Al$_2$O$_3$, Na/K/activated carbon, Cs/ZSM-5 and Ba/MCM-41.

Desulfurization (>98%) and denitrogenation (~100%) were achieved along with a significant level of metal (e.g., Mo) removals (>95%).

(5) Post Treatment: Selective Adsorption

Still another aliquot portion (40 mL) of the oxidized product was filtered to ensure that the solid material, if there is any, can be removed, and the resulting filtrate was subjected to the adsorption separation procedure by using active carbon fiber, silica gel and carbon molecular sieve (10 mL/g adsorbent).

Neither S nor N was detected in the final filtrate by conducting absorption treatment once or twice. In short, super deep desulfurization and denitrogenation were achieved in this run.

Similar results were achieved by using novel absorbents such as Pd/Al$_2$O$_3$, Pt/Al$_2$O$_3$, Pd/activated carbon, Pt/activated carbon, PdBaTiO$_3$, Pt/BaTiO$_3$, Pt/Mg$_2$Al$_2$O$_5$, Pd/MgAl$_2$O$_4$, V/Ce/MgAl$_2$O$_4$, V/Ce/MAl$_2$O$_4$ (M=Fe, Cr, Co, Ni, Cu, Cd, Hg, Zn, Zr), V/Ce/MgAl$_2$O$_4$.xAl$_2$O$_3$, M/MgAl$_2$O$_4$ (M=Fe, V, Cr, Ta, Nb, Ti, Mo, Zr, Mn), M/zeolite, M/activated carbon, M/activated carbon fiber, M/carbon molecular sieve, M/carbon nanotube (M=Fe, V, Cr, Ta, Nb, Ti, Mo, Zr, Mn) instead of the aforementioned conventional absorbent.

(6) Post Treatment: Selective Extraction Using Polar Solvent

A further aliquot portion (40 mL) of the oxidized product was filtered, and the filtrate was subjected to a selective extraction by using polar solvents such as N,N'-dimethylforamide (DMF), CH$_3$CN and organic acid.

As shown in Table 11, the results showed that remarkable desulfurization and denitrogenation were achieved by the treatment.

TABLE 11

| | S-compound | | N-compound | |
|---|---|---|---|---|
| Solvent | Unoxidized feed | Oxidized product | Unoxidized feed | Oxidized product |
| DMF | 0.07% | 0.007% | 40 ppm | <3 ppm |

(7) Post Treatment: Fractionation

A still further aliquot portion (40 mL) of the oxidized product was filtered, and the filtrate was subjected to a fractionation. The resids obtained at the highest boiling point of unoxidized resids were analyzed. The ascertained desulfurization (>90%) and denitrogenation (~100%) were achieved.

Example 8

Selective Oxidation of a Mixture of Hydrogenated LCO and Petroleum Resids (1) Selective Oxidation of Resids Using MC-TYPE Catalyst A selective oxidation was conducted by using a mixture of petroleum resides and hydrogenated LCO as a substrate in the presence of MC-type catalyst. The oxidized product was desulfurized by using a base catalyst.

The 480° C. plus residual bottoms of four kinds of crudes worldwide were mixed with hydrogenated LCO (0.07% S) in a mixing ratio of 25:75. The selective oxidation of this mixture was conducted in the presence of Co/Mn/HBr catalyst by using O$_2$/CO$_2$ (35%/65%) under the standard oxidation conditions.

Almost all the sulfur compounds in the residual bottoms were selectively oxidized into their corresponding sulfones (85-95% selectivity). 10-30% Carbonyl compounds were observed, which were mostly formed by the attack on the hydrocarbon moieties such as benzylic and allylic linkages, probably occurring subsequent to the sulfone formation.

(2) Post-Treatment: Pyrolysis

The oxidized resid bottom was subjected to pyrolysis in a 1 liter shaker bomb, and the results are listed in Table 12 below.

TABLE 12

| Resids | S(%) | Sufone(%) | Desulfurization(%) |
|---|---|---|---|
| 1 | 2.94 | 94.8 | 60.5 |
| 2 | 2.71 | 86.0 | 46.7 |
| 3 | 5.08 | 90.0 | 65.2 |
| 4 | 3.04 | 74.0 | 47.1 |

Remarkable desulfurization was achieved by a selective oxidation along with pyrolysis, while only pyrolysis without the selective oxidation pretreatment showed 10-15% of desulfurization.

It is believed that relatively low desulfurization results (47.1-65.2%) observed in this work is mainly due to the reversion of liberated H$_2$S/SO$_2$ to the sulfur compound in the substrate resid.

(3) Post-Treatment: Pyrolysis in the Presence of Base Catalyst (Optionally H-Donor Solvent)

In order to improve the desulfurization of the oxidized substrates, the pyrolysis was conducted in the co-presence of a hydrogen donor component and/or a base catalyst.

Another 288° C. plus Arabian crude resid was distilled into three fractions, e.g., IBP-288° C., 288-343° C., and 343° C. plus heavy bottoms, and were oxidized separately under the standard conditions. The resulting oxidized fractions were subjected to the base (KOH, Na/Al$_2$O$_3$) treatment for desulfurization. The results are presented in Table 13 below.

TABLE 13

| Distillation cut | 288° C.$^+$ RAC | | KOH treated* oxidized fraction | | |
|---|---|---|---|---|---|
| | oil, wt % | S wt % | oil | S | Desulf. % |
| IBP-288° C. | 5.6 | 0.45 | 9.3 | 0.12 | 73 |
| 288-343 | 14.7 | 1.30 | 10.7 | 0.26 | 80 |
| 343° C.$^+$ | 79.7 | 2.93 | 80.0 | 1.10 | 62 |

*The results over Na$_2$/Al$_2$O$_3$ see figures attached below

Scheme 8

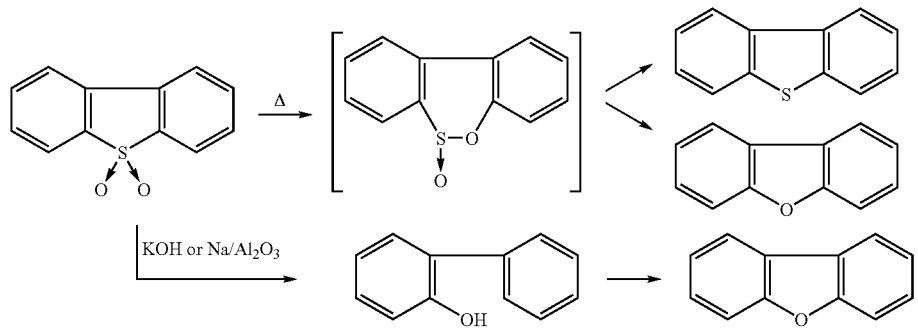

Further, a remarkable removal of N-moiety (to nearly zero %) and S-moiety (98-100%) were obtained by using a recently reported strong base material as below.

TABLE 14

| Base material | Desulfurization (%) |
|---|---|
| MgO•MgAl$_2$O$_4$ | 98 |
| $x$Al$_2$O$_3y$MgAl$_2$O$_4$ | 99 |
| Cs/ZSM-5 | ~100 |
| Cs/SiO$_2$ | ~100 |
| Ba/MCM-41 | ~100 |
| Zn—Al double-layered hydroxide | ~100 |
| AlGaPON | ~100 |
| Mg$_x$Ga$_{1-x}$(OH)$_2$(CO$_3$), x = 0.819 | ~100 |

As described above, a treatment by using a base such as KOH and Na$_2$O/Al$_2$O$_3$ optionally in the co-presence of H-donor solvent showed a remarkably improved desulfurization compared to a simple pyrolysis.

Meanwhile, a remarkable removal of metal contaminants (>89%) was also accompanied by the aforementioned post-treatments besides the desulfurization and the nitrogenation.

Further, it is noteworthy to mention that it was also ascertained that the level of four functions, i.e. desulfurization, denitrogenation, demetallation and production of oxygenates, may be controlled by varying the oxidant/S ratio. This is important in that it is required to modify the oxidation conditions to meet the environmental requirements of near zero S & N and 2.0-2.7% oxygen in the reformulated gasoline as well as future oxygenated diesel.

As described above, a process herein is a non-hydrogen process without causing any increasing cost due to the use of expensive hydrogen unlike in the conventional HDS process. A process herein also accomplishes deep or super deep desulfurization or denitrogenation, and it requires no such complex separation and/or removal process as in the conventional process. Moreover, a process herein also produces useful oxygenates at the same time via a one-pot reaction, without requiring an expensive hydrogenation process.

What is claimed is:

1. A one-pot process for reducing a sulfur- or a nitrogen-containing compound and producing an oxygenate in a hydrocarbon substrate, which comprises the steps of:
   (a) placing an MC-type homogeneous catalyst in a reactor;
   (b) adding the hydrocarbon substrate in the reactor; and
   (c) introducing an oxidant into the reactor;
   wherein the MC-type homogeneous catalyst is selected from the group consisting of Co/HBr, Mn/HBr, Co/Mn/HBr and Co/Mn/M'/HBr (M' is selected from the group consisting of K, Rb, Cs, Mo, Fe, Zr, Hf, Mn, Ti, Ni, Ru, Nb, Mo, W, Ta, Sb, Re, Rh, Pr, Sm, and Ce) and the oxidant is an O$_2$/CO$_2$ mixture.

2. The process according to claim 1, which further comprises the pretreatment step of removing a nitrogen-containing compound in the hydrocarbon substrate prior to the step (a).

3. A one-pot process for reducing a sulfur- or a nitrogen-containing compound and producing an oxygenate in a hydrocarbon substrate, which comprises:
   (a) placing an MC-type homogeneous catalyst in a biphasic system;
   (b) adding the hydrocarbon substrate in the biphasic system; and
   (c) introducing an oxidant into the biphasic system;
   wherein the MC-type homogeneous catalyst is selected from the group consisting of Co/HBr, Mn/HBr, Co/Mn/HBr and Co/Mn/M'/HBr (M' is selected from the group consisting of K, Rb, Cs, Mo, Fe, Zr, Hf, Mn, Ti, Ni, Ru, Nb, Mo, W, Ta, Sb, Re, Rh, Pr, Sm and Ce), and the oxidant is an O$_2$/CO$_2$ mixture.

4. A one-pot process for reducing a sulfur- or a nitrogen-containing compound and producing an oxygenate in a hydrocarbon substrate, which comprises:
  (a) converting the sulfur- or the nitrogen-containing compound in the hydrocarbon substrate into a sulfur- or a nitrogen-containing precursor, respectively, and also converting a benzylic or an allylic compound in the hydrocarbon substrate into the oxygenate at the same time via a selective oxidation of the hydrocarbon substrate in a biphasic system comprising an MC-type homogeneous catalyst and an oxidant; and
  (b) removing a layer that comprises the a sulfur- or a nitrogen-containing precursor;
  wherein the MC-type homogeneous catalyst is selected from the group consisting of Co/HBr, Mn/HBr, Co/Mn/HBr and Co/Mn/M'/HBr (M' is selected from the group consisting of K, Rb, Cs, Mo, Fe, Zr, Hf, Mn, Ti, Ni, Ru, Nb, Mo, W, Ta, Sb, Re, Rh, Pr, Sm and Ce), and the oxidant is an $O_2/CO_2$ mixture.

5. A one-pot process for reducing a sulfur- or a nitrogen-containing compound, a metal and producing an oxygenate in a hydrocarbon substrate, which comprises:
  (a) converting the sulfur- or the nitrogen-containing compound in the hydrocarbon substrate into a sulfur- or a nitrogen-containing precursor, respectively, and also converting a benzylic or an allylic compound in the hydrocarbon substrate into the oxygenate at the same time via a selective oxidation of the hydrocarbon substrate in the presence of an MC-type homogeneous catalyst and an oxidant; and
  (b) conducting a post-treatment selected from the group consisting of a filtration, a fractionation, a selective adsorption, a solvent extraction, a catalytic destruction, a selective oxidation, a pyrolysis and a combination thereof;
  wherein the MC-type homogeneous catalyst is selected from the group consisting of Co/HBr, Mn/HBr, Co/Mn/HBr and Co/Mn/M'/HBr (M' is selected from the group consisting of K, Rb, Cs, Mo, Fe, Zr, Hf, Mn, Ti, Ni, Ru, Nb, Mo, W, Ta, Sb, Re, Rh, Pr, Sm and Ce), and the oxidant is an $O_2/CO_2$ mixture.

6. The process according to claim 5, wherein the MC-type homogeneous catalyst is selected from the group consisting of Co/HBr, Mn/HBr, Co/Mn/HBr, Ni—Co/Mn/HBr and Zr—Co/Mn/HBr.

7. The process according to claim 5, wherein
  the benzylic or allylic compound is selected from the group consisting of tetralin; alkyltetralin derivative; partially hydrogenated naphthalene and naphthene; alkylbenzene derivative selected from the group consisting of xylene, cumene, isopropylbenzene, mesitylene, psuedocuemene and durene; and a mixture thereof; and
  the oxygenate is selected from the group consisting of alcohols, ketones, aldehydes, organic acid esters, aromatic or aliphatic organic acids, ethers and a mixture thereof.

8. The process of claim 5, wherein
  the sulfur-containing compound is selected from the group consisting of dialkyldibenzothiophene (4,6-DMDBT, 2,5-DMDBT), 4-alkyldibenzothiophene (4-MDBT), dibenzothiophene (DBT), alkylbenzothiophene, benzothiophene (BT), dialkylthiophene, thiophene, diphenylsulfide, thiophenol, methylphenylsulfide, alkyldisulfide and a mixture thereof; and
  the sulfur-containing precursor is a sulfoxide or a sulfone type oxygenate of the sulfur-containing compound.

9. The process of claim 5, wherein
  the nitrogen-containing compound is pyridine, quinoline, pyrrole, indole, carbazole, alkyl derivative thereof, aromatic and aliphatic amines thereof and a mixture thereof;
  the nitrogen-containing precursor is a N-oxide, an oxime, a nitron, a nitrosobenzene, a nitrobenzene or an indigo type oxygenate of the nitrogen-containing compound.

10. The process of claim 5, wherein the biphasic system is a nonpolar/polar system selected from the group consisting of oil/acetonitrile, oil/DMF, oil/acetic acid, oil/pyrrolidone, oil/NaOH aqueous solution, oil/$NaHCO_3$ aqueous solution, oil/$Na_2CO_3$ aqueous solution, oil/acetic acid-water mixture, oil/t-BuOH, oil/MeOH and a combination thereof.

11. The process according to claim 5, wherein the oxidation is performed at 140-190° C. under 10-15 atm.

12. The process according to claim 5, wherein
  the sulfur-containing compound and the nitrogen-containing compound are removed to less than 10 ppm and 5 ppm, respectively; and
  the oxygenate is produced in the amount of higher than 2.2-2.7 wt % on a basis of oxygen.

13. The process according to claim 5, wherein the hydrocarbon substrate is at least one selected from the group consisting of:
  (a) FCC product selected from the group consisting of gasoline, light cycle naphtha (LCN), heavy cycle naphtha (HCN), heavy oil fraction (middle distillate), light cycle oil (LCO), heavy cycle oil (HCO) and clarified oil (CLO);
  (b) hydrogenated (HDS or HDN) counterparts of (i) the FCC products;
  (c) heavy oil, bunker C oil or atmospheric and vacuum distilled resid bottoms;
  (d) asphaltene separated from crude oil;
  (e) long crude oil;
  (f) tar sand, oil sand or peat;
  (g) hydrogenated liquefied coal or H-coal;
  (h) chemically cleaned coal that underwent deashing, desulfurizing and denitrogenating processes; and
  (i) cokes, graphite or shale oil.

14. The process of claim 13, wherein the hydrocarbon substrate is a transportation fuel selected from the group consisting of:
  (a) a reformulated gasoline that has underwent desulfurization and denitrogenation through a hydrogenation process, followed by a selective oxidation for increasing the amount of oxygenates;
  (b) a light cycle oil, a heavy cycle oil, a heavy oil fraction or a mixture thereof that has underwent a hydrogenation; and
  (c) a reformulated diesel that has underwent desulfurization and denitrogenation through a hydrogenation process, followed by a selective oxidation for increasing the amount of oxygenates.

15. The process of claim 5, wherein the oxidant is an $O_2/CO_2$ mixture, and the volumetric ratio of $O_2/CO_2$ is 20-50%/80-50%.

16. The process of claim 15, wherein the volumetric ratio of $O_2/CO_2$ is 35-40%/65-60%.

17. The process of claim 15, wherein the volumetric ratio of $O_2/CO_2$ is 30-40%/70-60%.

18. The process of claim 17, wherein the $O_2/CO_2$ mixture comprises 5-30 vol % of helium or argon.

19. The process of claim 17, wherein the $O_2/CO_2$ mixture comprises less than 20 vol % of nitrogen.

* * * * *